United States Patent
Jezierski et al.

(10) Patent No.: US 11,040,133 B2
(45) Date of Patent: Jun. 22, 2021

(54) CLOSED LOOP SURGICAL SYSTEM

(71) Applicant: Smith & Nephew, Inc., Memphis, TN (US)

(72) Inventors: Rafal Jezierski, Middleton, MA (US); Brian Loreth, Braintree, MA (US)

(73) Assignee: Smith & Nephew, Inc., Memphis, TN (US)

( * ) Notice: Subject to any disclaimer, the term of this patent is extended or adjusted under 35 U.S.C. 154(b) by 573 days.

(21) Appl. No.: 15/305,294

(22) PCT Filed: May 12, 2015

(86) PCT No.: PCT/US2015/030299
§ 371 (c)(1),
(2) Date: Oct. 19, 2016

(87) PCT Pub. No.: WO2015/175484
PCT Pub. Date: Nov. 19, 2015

(65) Prior Publication Data
US 2017/0049952 A1 Feb. 23, 2017

Related U.S. Application Data

(60) Provisional application No. 61/991,827, filed on May 12, 2014.

(51) Int. Cl.
*A61M 3/02* (2006.01)
*A61M 1/00* (2006.01)
(Continued)

(52) U.S. Cl.
CPC ....... *A61M 3/022* (2014.02); *A61B 17/32002* (2013.01); *A61B 17/320016* (2013.01);
(Continued)

(58) Field of Classification Search
CPC ...... A61M 3/022; A61M 1617/320016; A61M 3/32002
See application file for complete search history.

(56) References Cited

U.S. PATENT DOCUMENTS 5,160,317 A 11/1992 Costin
5,630,798 A * 5/1997 Beiser ................ A61B 1/00135
604/30

(Continued)

FOREIGN PATENT DOCUMENTS

EP 1769756 4/2007
WO 2002017833 3/2002

OTHER PUBLICATIONS

Office Action dated Feb. 13, 2019 in corresponding Australian patent application No. 2015259400, 3 pages.
(Continued)

*Primary Examiner* — Nathan R Price
*Assistant Examiner* — Dung T Ulsh

(57) ABSTRACT

Featured is a closed loop surgical system including one or more control units that are configured to form a fluid control subsystem for fluid control and a device control subsystem for controlling a surgical device. The two control subsystems in combination provide an automatic self-managed closed loop system for the control of fluid into and out of the surgical site by means of intelligent communication and for maintaining a preselected pressure desired by the surgeon. In particular embodiments, this is accomplished by utilizing empirically correlated motor speed and load measurements, based on supplied current, from the surgical resection device when using its specific resection capability. For example, automatically adjusting fluid flow responsive to changes in loading of a surgical device or automatically sensing a load change for the surgical device during a surgical procedure
(Continued)

and automatically changing (increasing or decreasing) fluid flow responsive to the load change.

12 Claims, 9 Drawing Sheets

(51) Int. Cl.
    *A61B 17/32*         (2006.01)
    *A61B 17/00*         (2006.01)
    *A61B 90/00*         (2016.01)

(52) U.S. Cl.
    CPC ........ *A61M 1/0031* (2013.01); *A61M 1/0058* (2013.01); *A61M 3/0216* (2014.02); *A61B 2017/00017* (2013.01); *A61B 2017/00026* (2013.01); *A61B 2017/00075* (2013.01); *A61B 2090/064* (2016.02); *A61B 2090/066* (2016.02); *A61B 2217/005* (2013.01); *A61B 2217/007* (2013.01); *A61M 2205/3317* (2013.01); *A61M 2205/3331* (2013.01); *A61M 2205/3334* (2013.01); *A61M 2205/3365* (2013.01)

(56) References Cited

U.S. PATENT DOCUMENTS

| | | | |
|---|---|---|---|
| 5,779,662 A | 7/1998 | Berman | |
| 5,865,764 A | 2/1999 | Moorhead | |
| 6,159,160 A | 12/2000 | Hsei et al. | |
| 6,409,722 B1 * | 6/2002 | Hoey ................. | A61B 18/1206 |
| | | | 606/34 |
| 7,981,070 B2 | 7/2011 | McEwen | |
| 2002/0077587 A1 | 6/2002 | Boukhny et al. | |
| 2004/0133149 A1 | 7/2004 | Haischmann et al. | |
| 2004/0138687 A1 | 7/2004 | Himes | |
| 2008/0154182 A1 * | 6/2008 | Martin ................. | A61M 1/0072 |
| | | | 604/27 |
| 2010/0082053 A1 | 4/2010 | Hama et al. | |
| 2011/0224600 A1 * | 9/2011 | Orlandi ............... | A61M 3/0275 |
| | | | 604/30 |
| 2012/0016293 A1 | 1/2012 | Hayashi | |
| 2012/0172888 A1 * | 7/2012 | Shugrue ................. | A61B 17/42 |
| | | | 606/119 |
| 2013/0018400 A1 * | 1/2013 | Milton .................. | A61B 90/06 |
| | | | 606/167 |
| 2013/0204224 A1 * | 8/2013 | Muller-Pathle ..... | A61M 5/1452 |
| | | | 604/506 |
| 2014/0303551 A1 * | 10/2014 | Germain ............. | A61M 1/0058 |
| | | | 604/30 |
| 2015/0201956 A1 * | 7/2015 | Higgins ............. | A61B 17/3207 |
| | | | 606/159 |

OTHER PUBLICATIONS

International Search Report and Written Opinion for PCT Application No. PCT/US2015/030299, dated Aug. 28, 2015.
Office Action dated Jan. 22, 2019 in corresponding European patent application No. 15727116.4, 4 pages.
Office Action dated Jul. 27, 2018 in corresponding Chinese patent application 201580038043.1, 9 pages.
Chinese office action dated Apr. 16, 2019 in corresponding Chinese patent application 201580038043.1; 7 pages.
Chinese Patent Office, Decision of Rejection in corresponding Chinese application (201580038043.1), dated Aug. 7, 2019; 4 pages.
Japanese Application No. 2016-567620 Decision of Rejection dated Oct. 11, 2019.
Reexamination Notification dated Jan. 22, 2021.

\* cited by examiner

CLOSED LOOP SURGICAL SYSTEM

FIELD OF INVENTION

The present invention relates to surgical systems for use in connection with surgical endoscopy procedures and in particular, in arthroscopy procedures and more particularly to a closed loop surgical system for use with such surgical procedures that is capable of providing inflow and outflow control based on feedback from a surgical resection device, fluid flow and pressure sensing.

BACKGROUND OF THE INVENTION

There are many surgical systems in existence, which are used in endoscopy and in particular, in arthroscopy. These systems typically utilize a dedicated electric powered control unit 12 (FIG. 1) which includes a disposable tube set for open loop fluid flow control, a dedicated control unit 14 for a motor drive unit (MDU) 18 of a resection device for surgical resection. Such a conventional system 10 is basically configured as shown in FIG. 1. In use, the dedicated electric powered control unit 12 controls the flow of fluid from a fluid source 16 such as a bag of fluid. In such a conventional system the pump and resection devices communicate with each other in regard to the state of the MDU 14.

In such a conventional system, the effluent created by operation of the MDU is typically removed from the surgical site as it is being created by drawing the effluent and/or inflow from the surgical site to a suction source such as illustrated in FIG. 1. In the illustrated embodiment, the MDU is configured to sectional remove the effluent. The suction source can be any of a number of sources as are known in the art and otherwise appropriate for the intended use.

When the MDU 14 is on, the conventional system is operational and a pumping mechanism under the control of the electric powered control unit 12 increases flow to the surgical site to a set value. When the MDU is turned off the electric powered control unit 12 causes the flow of fluid to the surgical site to be decreased. The conventional system is not closed loop as the outflow and inflow from/to the surgical site are not both being automatically controlled.

In current fluid management systems, the outflow from the surgical site is typically controlled manually by the surgeon by their adjusting an outflow valve on the MDU. Presently, some units or systems combine outflow control and inflow control with the same unit. Pressure in the joint is calculated based on an algorithm and external pressure sampling.

Such endoscopic repair procedures typically embody a fluid source 16 that is coupled to a the pump so that the fluid can be pumped at a desired pressure/rate into the joint when a resection device is being used to cut, trim or otherwise process tissue and bone at or about the surgical site. At about the same time, a suctioning sub-system is typically engaged so as to remove the fluid and any debris from processing the tissue as well as any blood resulting therefrom (the outflow), from the surgical site. In addition this process of fluid flow and suctioning also can beneficially remove any blood, debris or other matter or liquid that may be occluding or clouding the endoscope and thus the view of the surgeon.

While the fluid source and/or fluid pump might be regulated to control the flow of fluid, these systems typically are arranged so that the surgeon or other surgical personnel (e.g., nurse) have to manually adjust the suction pressure during the procedure to increase or decrease the suction pressure and thus the amount of suctioning that is occurring. In addition, while fluid flow may be controlled so as to be at or about a desired value, if conditions change (e.g., more debris is being created than that being removed, the surgeon or other surgical personnel also must adjust the flow of fluid (inflow) to suit the changed conditions and also must adjust the suction pressure (controlling the outflow) as well to suit the changing conditions.

As can be seen from the foregoing, if the surgical procedure is creating more debris, there is no mechanism in place to detect this occurrence and automatically adjust the flow of fluid and suctioning to deal with the increased debris. In other words, these conventional systems require the surgeon to determine the presence or creation of the increased debris and then to take the appropriate actions to manually adjust fluid flow into the surgical site and suctioning from the surgical site. Correspondingly, when the amount of debris decreases the surgeon must take the appropriate actions to manually decrease fluid flow or suctioning so as to avoid unwanted operating conditions (e.g., raising of joint pressure to unwanted levels).

As this conventional system does not form a closed loop system, the surgeon or surgical personnel is required to monitor surgical conditions (e.g., visually) to determine if there is a need to adjust fluid inflow/outflow so as maintain a desired pressure within a joint as well as to deal with any clouding or occluding of the endoscope. In other words, while the surgeon is processing tissue using the resection device according to the surgical procedure, the surgeon is at the same time being distracted because of any such clouding or occluding and is also distracted because the surgeon also has to determine if the surgical conditions have changed warranting a manual adjustment to the fluid inflow/outflow while at the same time maintaining the joint pressure to a desired value.

If the surgeon determines that such adjustments are necessary, the surgeon or someone under his direction must make such adjustments. Thus, the surgeon is not able to focus on resection without having to worry at the same time about manipulating the inflow/outflow controls of the system to maintain joint pressure. As this process requires the surgeon to assess the operational conditions and to maintain joint pressure while resecting the tissue, the surgeon's actions also must take into consideration the effect such adjustments could have as to the distending of the joint and the potential for extravasation.

U.S. Publication No. 2008/0154182 appears to describe and teach an arthroscopic irrigation/aspiration system which may adjust flow to maintain the set pressure at the surgical site based on a code provided with the tubing set cassette for a given surgical procedure and a given surgical device used in the given procedure or, alternatively, based on a pressure and flow value as selected by the user on the control panel display (i.e., by up/down pressure/flow control buttons to set desired pressure and up/down flow rate). Such a pressure control system might provide information about pressure at the work site in order for inflow or outflow to be adjusted accordingly so as to be maintained at the set pressure.

U.S. Pat. No. 6,159,160 appears to show, teach or describe improved systems and methods that are used for controlled infusion of fluid into a body cavity. In particular, such a system approach allows a user to control pressure created in a body cavity over a broad range of fluid flow rates required in various medical procedures. It is further provided that the methods and systems thereof are particularly well adapted for minimally invasive endoscopic procedures requiring controlled infusion of fluid into a body cavity, such as for hysteroscopic endometrial resection, transurethral resection, and various laparoscopic or arthroscopic procedures performed inside a patient. It is specifically noted therein that such systems and methods are described in the context of a uterine resection procedure.

U.S. Publication No. 2004/0133149 (which corresponds to U.S. Pat. No. 7,371,224) appears to show, teach or describe a device for rinsing a body cavity with a fluid. Such a device includes a rinse pump for introducing fluid into a body cavity and a pressure sensor on a pressure side of the rinse pump.

U.S. Publication No. 2012/0172888 (which corresponds to U.S. Pat. No. 8,568,424) appears to show, teach or describe a hysteroscopic tissue removal system. Hysteroscopy is the inspection of the uterine cavity by endoscope or hysteroscope with access through the cervix.

U.S. Publication No. 2007/020148 (which corresponds to U.S. Pat. No. 7,981,070) appears to show, teach or describe an internal tourniquet for establishing hemostasis within a portion of a limb to facilitate surgery.

U.S. Pat. No. 5,865,764 appears to show, teach or describe a device and method for non-invasive measurement of internal pressure within body cavities. In more specific aspects, this patent is more particularly directed to a device and method for non-invasive measurement of intraocular pressure during an operation on an eye.

U.S. Pat. No. 5,779,662 appears to show, teach or describe a laparoscopic tissue resection system, more particularly a powered laparoscopic tissue resection system/procedures in which a body cavity is filled with a gas medium to maintain pneumoperitoneum. While this patent refers to the general term fluid it should be recognized that the fluid is specifically a gas. Such a powered tissue resection system for use during endoscopic surgical procedures includes a powered tissue resection device that simultaneously resects and aspirates tissue from the surgical work site within the gas-filled body cavity. A portion of the ambient fluid medium (i.e., from the gas-filled body cavity) is aspirated along with the aspirated tissue. A separating means is provided to separate the resected tissue and other debris from the fluid medium, generally carbon dioxide, so that the separated fluid medium can be returned to the body cavity to maintain pneumoperitoneum.

U.S. Publication No. 2004/0138687 (which corresponds to U.S. Pat. No. 7,717,931) appears to show, teach or describe a surgical tool system with a handpiece having a valve assembly for regulating the fluid pump connected to the handpiece. In general, this patent shows, teaches and describes a powered surgical handpiece such as those employed in endoscopic surgery. More particularly, such a powered surgical handpiece includes an irrigator for applying fluid to a surgical site, a suction conduit for drawing fluid from the site, a means for clearing the suction conduit and a motor for actuating a complementary cutting accessory.

U.S. Publication No. 2012/0016293 appears to show, teach or an endoscope gas delivery system including two gas supply sources (e.g., carbon dioxide and air sources—an air pump and a carbon dioxide gas cylinder) and where the gases are smoothly and automatically switched. By using a gas supply flow rate-adjusting unit; a carbon dioxide gas is supplied to an endoscope. When the remaining amount of the carbon dioxide gas of the cylinder is detected and the detected pressure of the carbon dioxide gas becomes less than a predetermined value, the air pump is rotated to supply pressurized air. The rotation number of the air pump is controlled, and the same amount of pressurized air is supplied as that of the supplied carbon dioxide gas. This switching to the pressurized air is automatically performed. The supply amounts before and after the switching become equal to each other, and a surgical operator does not feel any discomfort.

European Patent No. 1769756 ("EP '756 Patent") appears to show, teach or describe a surgical instrument for endoscopic or laparoscopic insertion into a surgical site for simultaneous stapling and severing of tissue. This EP patent appears to show, teach or describe a surgical instrument that can be endoscopically or laparoscopically inserted into a surgical site for simultaneous stapling and severing of tissue. The surgical instrument includes load sensing pressure transducers that are strategically placed for closed loop control and monitoring. Such load sensing within the staple applying assembly (end effector) may provide feedback to prevent firing of a staple if there is insufficient or too much tissue. Such load sensing also allows for sensing appropriate presence buttress material and to deploy the buttress material after firing is sensed.

U.S. Publication No. 2002/0077587 is directed to an infusion control system having a flexible, collapsible infusion container. More specifically, this publication appears to show, teach or describe an infusion control system having a flexible, collapsible infusion container for use in the field of cataract surgery and more particularly to an infusion control system for a phacoemulsification handpiece. In this surgery, a device is inserted into a portion of the eye to breakdown the lens and the broken-down lens is then aspirated so an artificial intraocular lens can be inserted into the eye.

U.S. Publication No. 2010/0082053 appears to show, teach or describe a fluid ejection device, fluid ejection method and a fluid ejection surgical instrument that advantageously can more surely eject fluid with high precision when the fluid is ejected to a target site. As further described, such a fluid ejection device or fluid ejection surgical instrument is configured so as to selectively and controllable eject repetitive fluid pulses at a high pressure that can be used to selectively cut certain tissue and also to selectively not cut other tissue.

It thus would be desirable to provide a closed loop surgical system and methods related thereto. It would be particularly desirable to provide such a system and method that would be capable of automatically adjusting fluid flow responsive to changes in the loading of a resection device. It also would be desirable to provide such a system and method that would be capable of automatically sensing a load change for a given resection device during the conduct of the surgical procedure and automatically changing (increasing or decreasing) fluid flow responsive to such a load change. Further, it would be desirable to provide such a system and method that would be capable of automatically determining current flow changes to an electric motor of the resection device, relating these current changes to a load change and automatically changing (increasing or decreasing) fluid flow (inflow and/or outflow) responsive to such a current or load change.

SUMMARY OF THE INVENTION

The present invention features, in its broadest aspects a closed loop surgical system including one or more control units that are configured to form a fluid control subsystem for fluid control and a device control subsystem for controlling a surgical device. The two control subsystems in combination provide an automatic self-managed closed loop system for the control of fluid into and out of the surgical site by means of intelligent communication and for maintaining a preselected pressure desired by the surgeon. In particular embodiments, this is accomplished by utilizing empirically correlated motor speed and load measurements, based on supplied current, from the surgical resection device when using its specific resection capability. For example, automatically adjusting fluid flow responsive to changes in loading of a surgical device or automatically sensing a load change for the surgical device during a surgical procedure and automatically changing (increasing or decreasing) fluid flow (inflow and/or outflow) responsive to the load change. Also featured are methods related thereto.

According to one aspect of the present invention there is featured a closed loop surgical system for use in endoscopic surgical procedures such as arthroscopic surgical procedures.

Such a closed loop surgical system, more particularly includes two control sub-systems, a fluid control subsystem including a fluid controller that is configured and arranged so as to control flow of fluid and a device control subsystem including a device controller that is configured and arranged so as to control the surgical device. The fluid controller is further configured and arranged so as to control the fluid going to the surgical site (fluid inflow) and the fluid being suctioned or extracted from the surgical site (fluid outflow), where one or both of the inflow or outflow is controlled so as to maintain a desired pressure within the joint. The device controller also monitors as least one parameter of the surgical device. It also is within the scope of the present invention to provide a single controller that is configured and arranged so to be capable of performing the functions as described herein for both the fluid controller and the device controller.

One of the fluid controller or the device controller determines from the one parameter being monitored if the operational conditions for the surgical device have changed; further determines if the changed operation condition requires a change in one or both of fluid inflow or fluid outflow; and if it is determined that there is change needed to inflow and/or outflow, determining the flow change. The fluid controller also is further configured and arranged so as to cause the fluid flow to be one of increased or decreased based on the determined flow change.

In an embodiment of the present invention, the fluid control subsystem and the device control subsystem in combination provide an automatic self-managed closed loop system for the control of fluid into and out of the surgical site by means of intelligent communication.

In a further embodiment, the fluid controller is further configured and arranged so as to at least maintain a preselected pressure at a surgical site.

In yet further embodiments, the fluid controller is further configured an arranged so as to maintain the preselected pressure by utilizing empirically correlated motor speed and load measurements, based on supplied current, from the surgical device when using its specific resection capability.

In yet further embodiments, the closed loop surgical system further includes an inflow pump, an outflow pump and a fluid source. The fluid source is coupled to the inflow pump and each of the inflow and outflow pumps are fluidly coupled to the surgical site. The fluid controller also is configured and arranged so as to control operation of one or both of the inflow pump and the outflow pump so as to at least maintain a preselected pressure in an area at the surgical site.

In yet further embodiments, the fluid controller is configured and arranged so as to automatically adjust fluid flow responsive to changes in the loading of the surgical device.

In yet further embodiments, the device controller is configured and arranged so as to automatically sensing a load change for a given resection device during the conduct of the surgical procedure and the fluid controller is configured and arranged so as to automatically change (increasing or decreasing) fluid flow responsive to such a load change.

In yet further embodiments, the device controller is configured and arranged so as to automatically determine current flow changes to an electric motor of the resection device, relating these current changes to a load change and the fluid controller is configured and arranged so as to automatically change (increasing or decreasing) fluid flow (inflow and/or outflow) responsive to such a determined current or load change.

According to another aspect of the present invention there is featured a method that automatically controls flow of fluid into and out of a surgical site during a surgical procedure for example, endoscopic surgical procedures including arthroscopic surgical procedures. Such a method for automatically controlling flow of fluid into and out of a surgical site includes providing two control systems, a fluid control system including a fluid controller that is configured and arranged so as to control flow of fluid and a device control system including a device controller that is configured and arranged so as to control the surgical device. The provided fluid controller is further configured and arranged so as to control the fluid going to the surgical site (fluid inflow) and the fluid being suctioned or extracted from the surgical site (fluid outflow), one of the inflow or outflow being controlled so as to maintain a desired pressure within the joint. Also, the provided device controller is configured and arranged so as to monitor as least one parameter of the surgical device.

One of the provided fluid controller or the provided device controller is further configured and arranged to determine from the one parameter if operational conditions for a surgical device have changed, determine if the changed operation condition requires a change in one or both of fluid inflow or fluid outflow respectively to/from the surgical site; and if it is determined that there is change needed to inflow and/or outflow, determining the flow change. Further, the provided fluid controller is further configured and arranged so as to cause the fluid flow to be one of increased or decreased based on the determined flow change.

In an embodiment of the present invention, the fluid control system and the device control system in combination provide an automatic self-managed closed loop for the control of fluid into and out of the surgical site by means of intelligent communication.

In yet another embodiment, the provided fluid controller is further configured and arranged so as to at least maintain a preselected pressure at a surgical site. Additionally, the provided fluid controller is further configured an arranged so as to maintain the preselected pressure by utilizing empirically correlated motor speed and load measurements, based on supplied current, from the surgical resection device when using its specific resection capability.

In yet another embodiment, the method further includes providing an inflow pump, an outflow pump and a fluid source, where the fluid source is coupled to the inflow pump; where each of the inflow and outflow pumps are fluidly coupled to the surgical site. Also, the provided fluid controller controls operation of one or both of the inflow pump and the outflow pump so as to at least maintain a preselected pressure in an area at the surgical site.

In yet a further embodiment the provided fluid controller is further configured and arranged so as to automatically adjust fluid flow responsive to changes in the loading of the surgical device.

In yet a further embodiment, the provided device controller is further configured and arranged so as to automatically sense a load change for a given resection device during the conduct of the surgical procedure. Further, the provided fluid controller automatically changes (increasing or decreasing) fluid flow responsive to such a load change.

In yet a further embodiment, the provided device controller is configured and arranged so as to automatically determine current flow changes to an electric motor of the resection device, relating these current changes to a load change. Further, the provided fluid controller automatically changes (increasing or decreasing) fluid flow (inflow and/or outflow) responsive to such a determined current or load change.

According to yet another aspect of the present invention there is featured another method that automatically controls flow of fluid into and out of a surgical site during a surgical procedure for example, endoscopic surgical procedures including arthroscopic surgical procedures. Such a method includes monitoring operation of a surgical device in operation during the surgical procedure and detecting at least one operational parameter/characteristic of the surgical device. Such a method further includes evaluating the detected parameter/characteristic to determine if the evaluated operational parameter/characteristic represent a changing value and if a change is determined, then the process proceeds with evaluating the change characteristic/parameter to determine if the flow of fluid into and/or out of the surgical site should be adjusted. Such a method further includes providing one or more outputs to adjust (increase or decrease) the flow of fluid at least one of into or out of the surgical to a new value.

In an embodiment, such a method further includes providing positive drive pump devices for each of the flows into and out of the surgical site. Such providing includes providing one or more outputs to at least one of the positive drive pump device for each of the flows into and out of the surgical site so as to respectively adjust the determined flow of fluid into and/or out of the surgical site that is determined to be adjusted.

In yet a further embodiment, the surgical device includes a resection device having an electrical motor. Also, such monitoring includes monitoring electrical power characteristics of the electrical motor and such detecting includes detecting a change in power consumption. Further, such a method further includes determining if the detected change is indicative of a changing motor load and wherein such a method further includes adjusting one or both of the flows into and out of the surgical site responsive to the changing motor load.

In yet a further embodiment, such monitoring and detecting includes monitoring more than one operational parameter and/or operational characteristic such as flow, current and pressure and detecting an operational parameter and/or operational characteristic for each being monitored. Also, such evaluating includes evaluating each of the detected operational parameters/characteristics to determine to determine if the operational parameter/characteristic being evaluated represents a changing value. If one or more changing values is determined, then the process proceeds with evaluating the changed characteristic/parameters to determine if the flow of fluid into and/or out of the surgical site should be adjusted.

According to yet another aspect of the present invention there is featured a control system that automatically controls flow of fluid into and out of a surgical site during a surgical procedure for example, endoscopic surgical procedures including arthroscopic surgical procedures. Such a control system includes one or more computing mechanisms or computing devices as are known to those skilled in the art (e.g., processors, microprocessors or ASICs) as well as related devices (e.g., memory and storage device(s)) and an applications or software program for execution on each of the one or more computing mechanisms. Such an applications or software program further includes instructions, criteria, data and/or code segments for carrying out the methods, method steps and operations described herein. In one embodiment, the computing system includes one computing mechanism and one or more an applications programs.

In further embodiments, such an applications or software program includes instructions, criteria, data and/or code segments to form a closed loop surgical system including two control sub-systems; a fluid control subsystem for fluid control and a device control subsystem for controlling the surgical device. These two control subsystems in combination provide an automatic self-managed closed loop system for the control of fluid into and out of the surgical site (inflow and outflow respectively) by means of intelligent communication.

In yet further embodiments, such an applications or software program further includes instructions, criteria, data and/or code segments so as to automatically adjust fluid flow into and/or out of the surgical site responsive to changes in the loading of the surgical device, more particularly, automatically sensing a load change for a given surgical device during the conduct of the surgical procedure and automatically changing (increasing or decreasing) fluid flow responsive to such a load change; or (c) automatically determining current flow changes to an electric motor of the surgical device, relating these current changes to a load change and automatically changing (increasing or decreasing) fluid flow (inflow and/or outflow) responsive to such a current or load change.

According to yet another aspect of the present invention there is featured a computer readable storage medium control on which is stored system one or more applications or software programs that are configured and arranged so as to automatically control flow of fluid into and out of a surgical site during a surgical procedure for example, endoscopic surgical procedures including arthroscopic surgical procedures. In further embodiments, such a computer readable storage medium is non-transitory. Such one or more applications or software program further includes instructions, criteria, data and/or code segments for carrying out the methods, method steps and operations described herein.

In further embodiments, such an applications or software program includes instructions, criteria, data and/or code segments to form a closed loop surgical system including two control sub-systems; a fluid control subsystem for fluid control and a device control subsystem for controlling the surgical device. These two control subsystems in combination provide an automatic self-managed closed loop system for the control of fluid into and out of the surgical site (inflow and outflow respectively) by means of intelligent communication.

In yet further embodiments, such an applications or software program further includes instructions, criteria, data and/or code segments so as to automatically adjust fluid flow into and/or out of the surgical site responsive to changes in the loading of the surgical device, more particularly, automatically sensing a load change for a given surgical device during the conduct of the surgical procedure and automatically changing (increasing or decreasing) fluid flow responsive to such a load change; or (c) automatically determining current flow changes to an electric motor of the surgical device, relating these current changes to a load change and automatically changing (increasing or decreasing) fluid flow (inflow and/or outflow) responsive to such a current or load change.

Other aspects and embodiments of the invention are discussed below.

DEFINITIONS

The instant invention is most clearly understood with reference to the following definitions:

USP shall be understood to mean U.S. Patent Number and U.S. Publication No. shall be understood to mean U.S. Published Patent Application Number.

The terms "comprising" and "including, as used in the discussion directed to the present invention and the claims are used in an open-ended fashion and thus should be interpreted to mean "including, but not limited to." Also the terms "couple" or "couples" is intended to mean either an indirect or direct connection. Thus if a first component is coupled to a second component, that connection may be through a direct connection, or through an indirect connection via other components, devices and connections. Further the terms "axial" and "axially" generally mean along or substantially parallel to a central or longitudinal axis, while the terms "radial" and "radially" generally mean perpendicular to a central, longitudinal axis.

Additionally directional terms such as "above," "below," "upper," "lower," etc. are used for convenience in referring to the accompanying drawing figures. In general, "above," "upper," "upward" and similar terms refer to a direction toward a proximal end of an instrument, device, apparatus or system and "below," "lower," "downward," and similar terms refer to a direction toward a distal end of an instrument, device, apparatus or system, but is meant for illustrative purposes only and the terms are not meant to limit the disclosure.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

As used herein the terms "cutting" or "cut" when used in describing the methods, instruments or apparatus of the present invention shall be understood to be inclusive of any of a number of techniques or operations know in the art for surgically working bone, cartilage or tissue such techniques include but are not limited to trimming, shaping, resecting, abrading or grinding of bone or tissue.

The term tissue when used hereinafter shall be understood to include other parts or structure of a human body including, but not limited to cartilage, muscle, bone, bony structures (e.g., vertebrae) and ligaments.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Before the present invention is described in detail, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Figure 1:
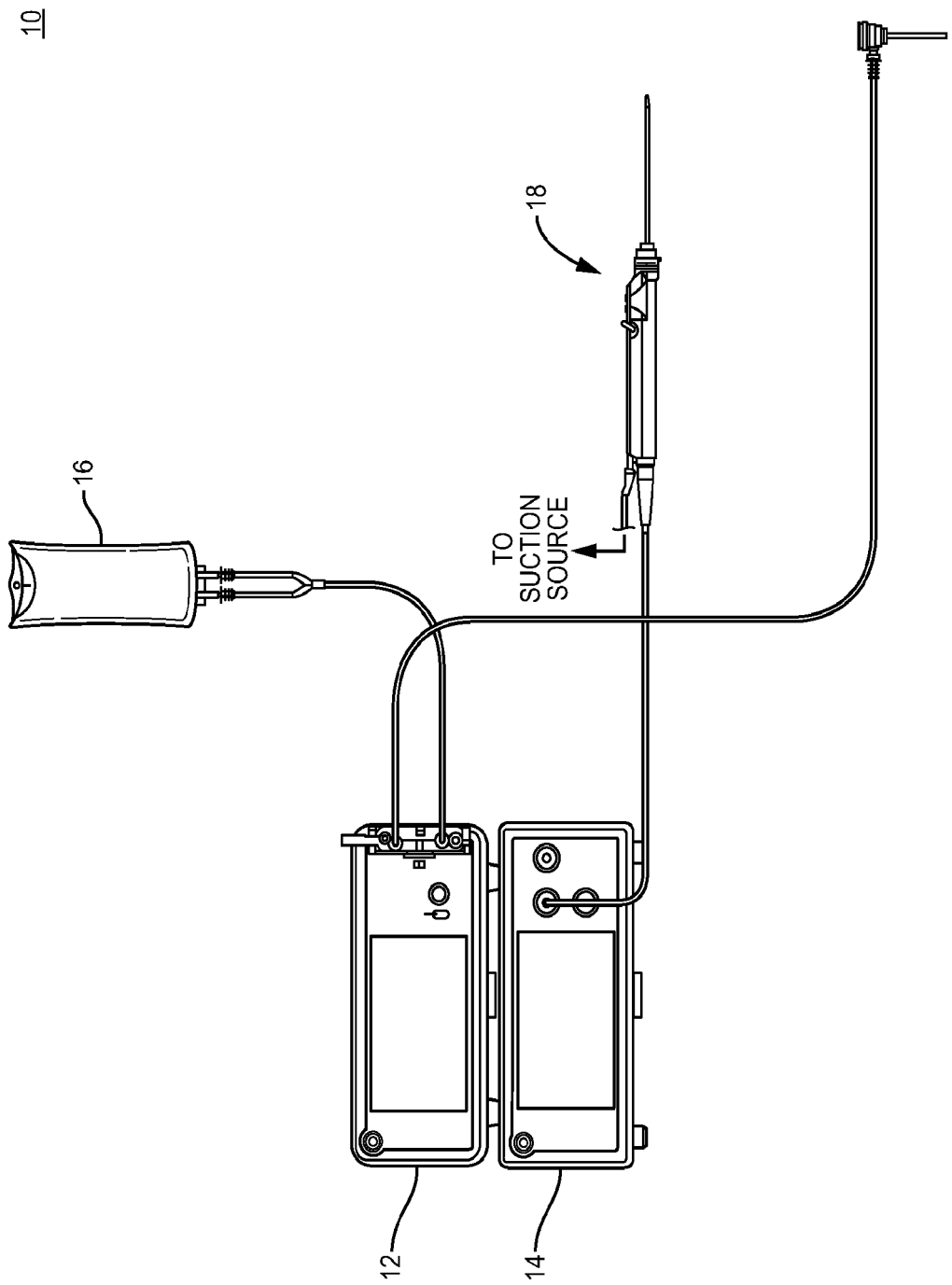
FIG. 1 is a schematic view of a conventional surgical system.
Figure 2A:
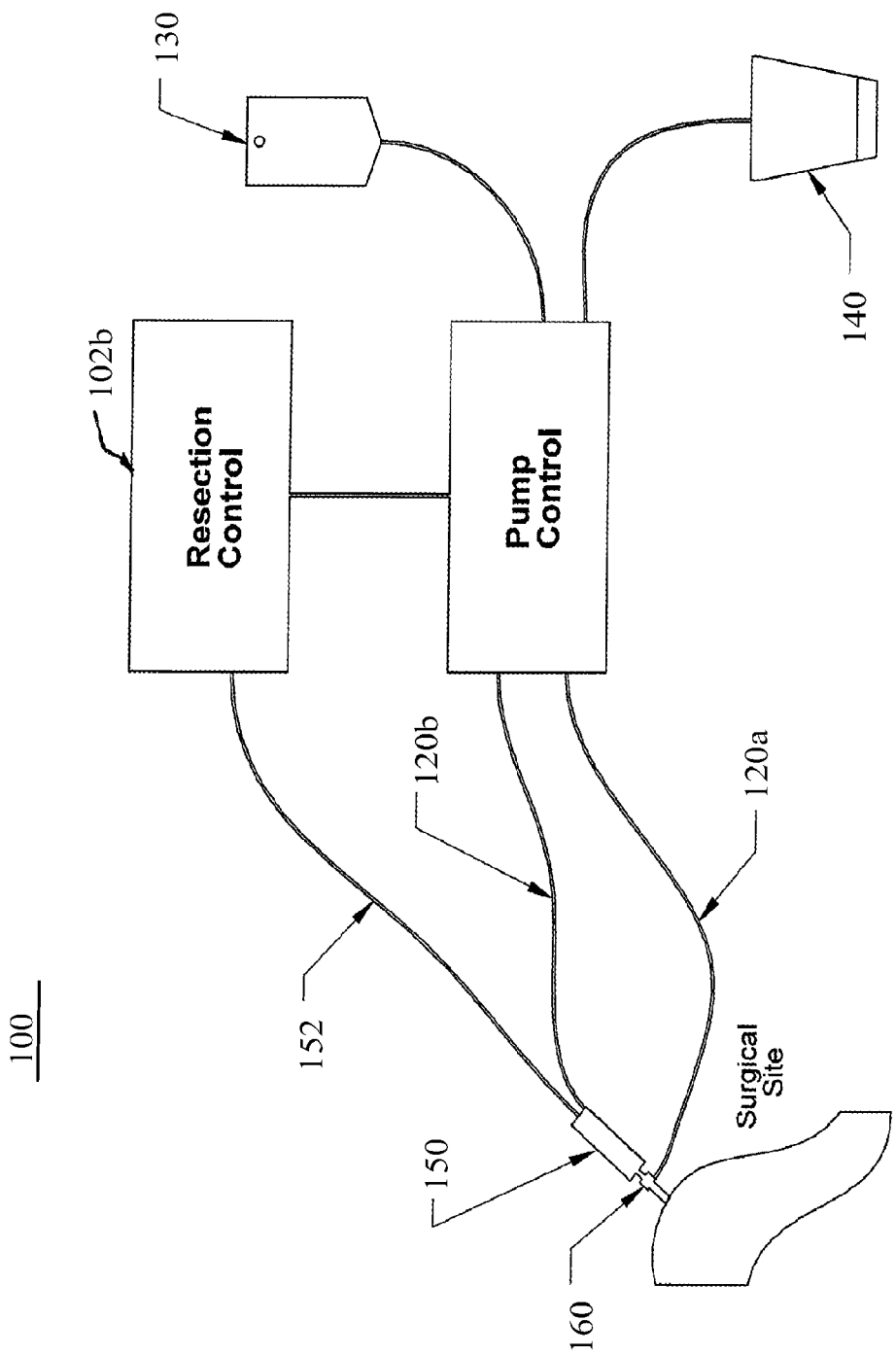
FIG. 2A is a schematic view of a closed loop surgical system according to the present invention.
Figure 2B:
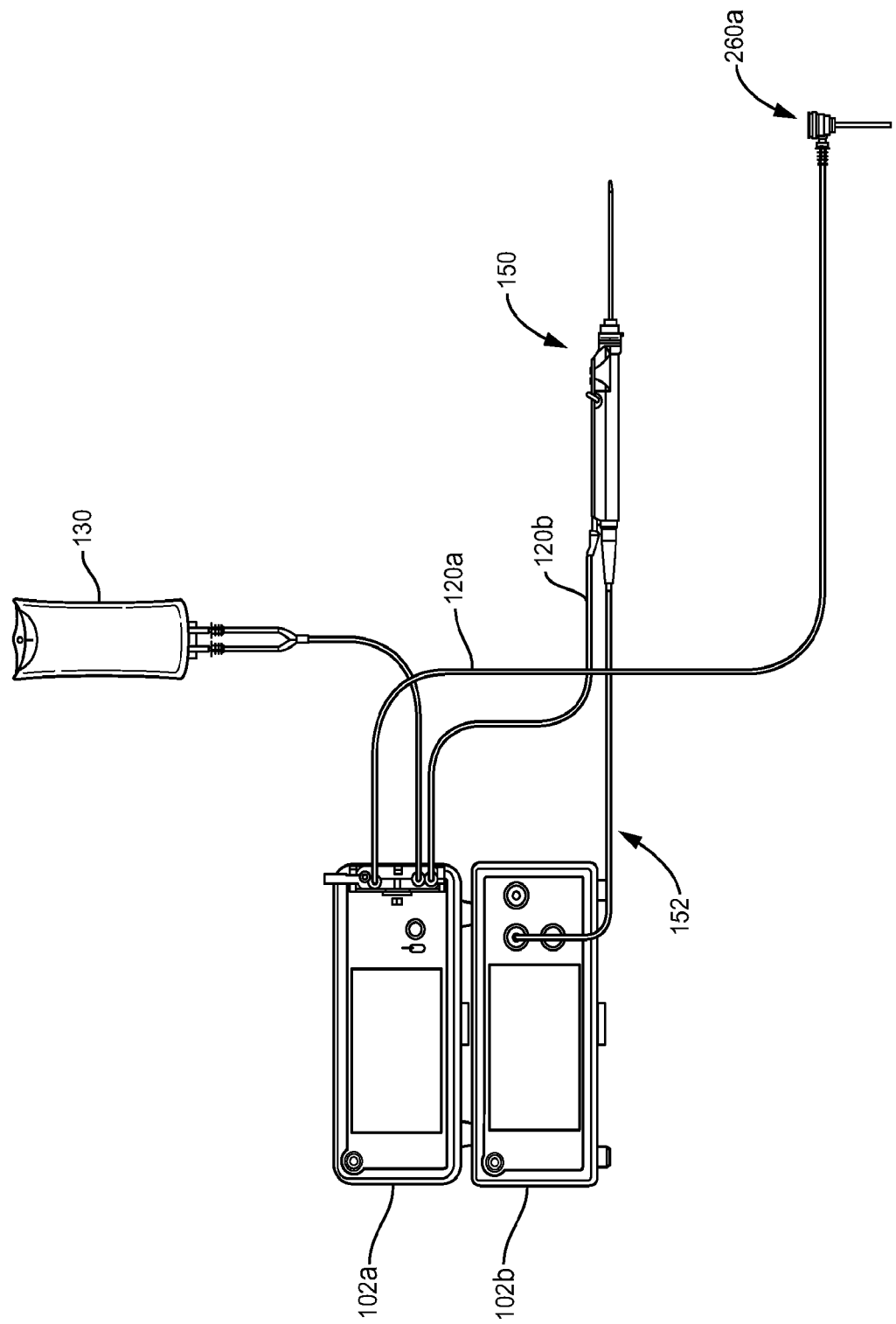
FIG. 2B is an illustrative block diagram view of the closed loop surgical system according to another embodiment of the present invention.
Figure 5:
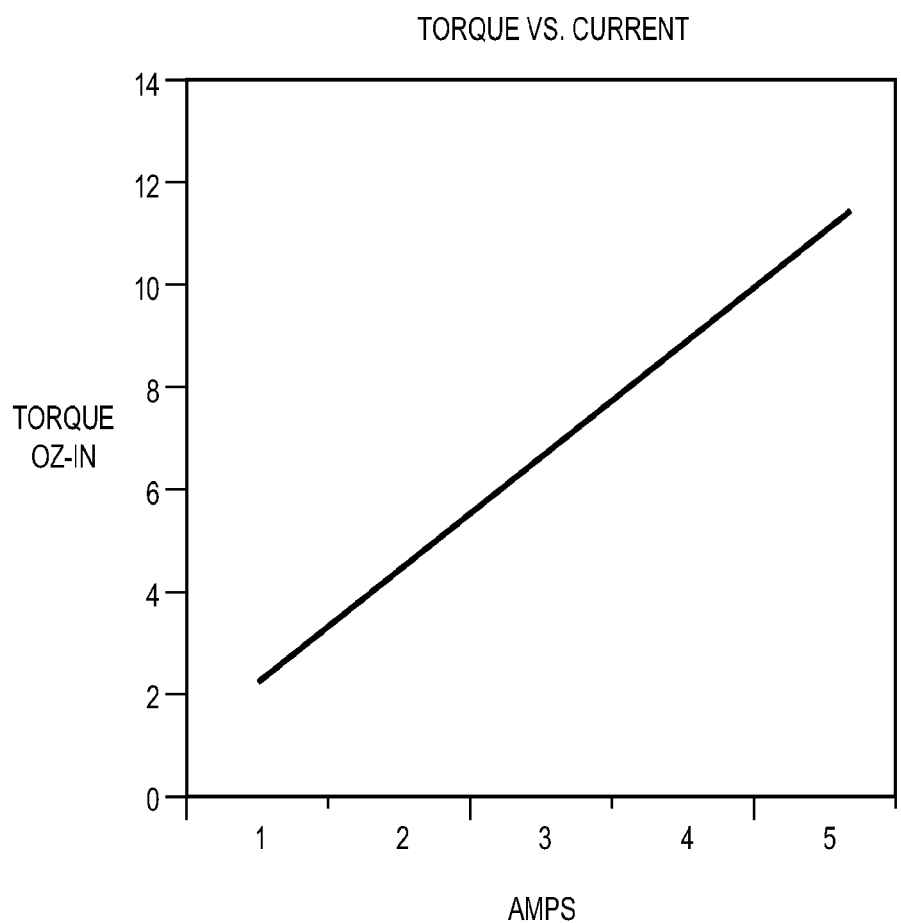
FIG. 5 is a graphical view of a typical relationship between torque and supplied current for a motor used in such a system.

Referring now to the various figures of the drawing wherein like reference characters refer to like parts, there is shown a schematic view of a closed loop surgical system 100 according to the present invention (FIG. 2A); an illustrative block diagram view of the closed loop surgical system 100 of FIG. 2A (FIG. 2B); an illustrative control unit for providing motor and fluid control according to the present invention (FIG. 3); and a graphical view of a typical relationship between torque and supplied current for a motor used in such a system (FIG. 5). As shown in FIGS. 2A, B, such a closed loop surgical system 100 according to the present invention is capable of providing inflow and outflow control based on feedback from a surgical resection device 150, fluid flow and pressure sensing. Such a system(s) is/are for use in connection with in surgical endoscopy procedures and in particular, in arthroscopy procedures.

As described further herein, such a closed loop surgical system 100 also is preferably configured and arranged so that it can automatically adjust fluid flow responsive to changes in the loading of a resection device 150, more particularly, automatically sensing a load change for a given resection device during the conduct of the surgical procedure and automatically changing (increasing or decreasing) fluid flow responsive to such a load change; or (c) automatically determining current flow changes to an electric motor of the resection device, relating these current changes to a load change and automatically changing (increasing or decreasing) fluid flow (inflow and/or outflow) responsive to such a current or load change.

Such a closed loop surgical system 100 includes one or more control units 102a, b that are configured and arranged so as form two control sub-systems 110a, b; a fluid control subsystem 110a for fluid control and a device control subsystem 110b for controlling the surgical resection device. These two control subsystems in combination provide an automatic self-managed closed loop system for the control of fluid into and out of the surgical site (inflow and outflow respectively) by means of intelligent communication. The fluid system control is based on maintaining a preselected pressure desired by the surgeon. In particular embodiments, this is accomplished by utilizing empirically correlated motor speed and load measurements, based on supplied current, from the surgical resection device when using its specific resection capability (e.g., trimming or cutting tissue, one or the like.

When dealing with endoscopic or arthroscopic surgical procedures involving joints, one controls the fluid going to the surgical site (fluid inflow 120a) and the fluid being suctioned or extracted from the surgical site (fluid outflow 120b) so as to maintain a desired pressure within the joint, such that the joint is distended for access and so as to keep the endoscope or arthroscope clean so the surgeon can visualize the surgical site. However, care must be taken to guard against overpressure of the joint as this can lead to an undesirable distending of the joint and to deleterious extravasation of fluid into the patient. Thus, the one or more control units of the proposed approach are configured and arranged so as to significantly decrease, if not prevent the potential for such undesirable distending of the joint and deleterious extravasation of fluid.

More particularly, the one or more control units are configured and arranged to provide a motor control subsystem 110b including a motor control unit 102b to control operation of the resection device and a fluid control subsystem 110a including a fluid control unit 102a that controls fluid inflow 120a and fluid outflow 120b so as to maintain a desired pressure in the area of the surgical site. As illustration, such a system 100 also includes a source of fluid 130 such as a bag of saline solution or the like and an inflow pump 104 (FIG. 3) such as a positive drive pump for example a centrifugal or peristaltic pump, which pump is fluidly coupled to the fluid source and the surgical site.

In more particular aspects, the resection device 100 is configured and arranged with a fluid discharge line (e.g., fluid inflow 120a) that is fluidly coupled to the inflow pump 104 (e.g., a centrifugal or peristaltic pump). The distal end of such a discharge line is positioned in proximity to the surgical site when the resection device is located within the body in connection with the surgical procedure. In more particular embodiments, at least a portion of the resection device 100 is inserted through a cannula 160. The cannula 160 is fluidly coupled to the fluid inflow 120a using any of a number of techniques known in the art so that the fluid inflow 120a passes through the cannula and thence to the surgical site. The inflow pump 104 also is operably coupled to the fluid control subsystem/control unit (110b/102b) so that the subsystem/control unit can control the flow of fluid to the surgical site (i.e., fluid inflow 120a).

In alternative embodiments and as generally described in U.S. Pat. No. 5,759,185 (the teachings of which are incorporated herein by reference; see FIG. 6 thereof), the operational or distal end of the resection device 150 is introduced through a puncture wound in the body which accesses the surgical site and so that the operable or distal end of the resection device is located proximal the surgical site. An endoscope also is inserted through a second puncture wound which both provides illumination (from a light source) to the surgical site and conveys an image of the surgical site to a television camera. The image is delivered by the camera to a display device such as a television screen for viewing by the surgeon. Alternatively, the surgeon may view the image using an eyepiece on the endoscope and/or the image can be recorded.

A cannula or other device (e.g., a tubular device) 260a (FIG. 2B) as is known in the art is introduced into the body through a third puncture wound which as described herein is coupled to a fluid source via the inflow pump 104. The fluid inflow 120a flows via this other device 260a and thence to the surgical site to irrigate the surgical site and provide a medium by which effluent created by the operation of the resection device is drawn into the outflow 120b as described further herein.

The surgical site also is fluidly coupled to an outflow pump 106, such as a positive drive pump, for example a centrifugal or peristaltic pump. Alternatively, the surgical site is fluidly coupled to a valve (e.g., a mechanically controlled valve) and a suction source (e.g., external suction source) as described further herein. In more particular aspects, the resection device 150 is configured and arranged with a suction or aspiration line that is fluidly coupled to the outflow pump 106 or the mechanical valve via the fluid outflow 120b. The distal end of such a suction line is positioned in proximity to the surgical site when the resection device 150 is located within the body in connection with the surgical procedure. In more particular embodiments, the resection device 150 is further configured so as to include a connection to fluidly couple the suction line and the fluid outflow 120b. In use, the pump or the valve in combination with the suction source, is fluidly coupled to a waste receptacle 140 so that any fluid discharge from the surgical site, including any blood or tissue debris, can be properly received in the waste receptacle, outside of the body for proper disposal. This discharge also is referred to herein as the fluid outflow.

As described herein, one of, or both of, the inflow and outflow pumps 104, 106 are operably coupled to the fluid control subsystem/control unit (110a/102a) to control the inflow and outflow of fluid so as to maintain a pressure in the joint as desired by the surgeon. In other words, the fluid control subsystem/unit automatically balances the fluid inflow and fluid outflow to maintain this pressure, particularly when the resection device is in operation. In more particular embodiments, the fluid control subsystem/unit (e.g., pump control) utilizes an algorithm or the like which is responsive to pressure and/or flow sensors to maintain this balance.

The fluid control subsystem/unit (110a/102a) and the motor control system/control unit (110b/102b) also are configured so as to generate an output that is representative of an operational characteristic or parameter of the resection device (e.g., motor torque) and using this output, determining if the fluid inflow and fluid should be adjusted (e.g., increased/decreased) to account for changing operational conditions of the resection device.

In more particular aspects, the motor control subsystem/control unit (110b/102b) is controls operation (e.g., resection control) of an electric motor of the motor drive unit via a motor control cable 152. The motor control cable is used to control the supply of electricity to the electric motor responsive to control inputs by the surgeon and also so as to maintain the rotational speed of the motor. The motor control subsystem/control unit (110b/102b) also is configured so as to provide an output signal that is representative of the load on the resection device and the fluid control subsystem/control unit is configured to determine if the fluid inflow and fluid outflow (120a, b) should be adjusted to either increase or decrease the fluid inflow and/or the fluid outflow responsive to the changing motor load. For example, if the motor load has increased or is increasing, the fluid control subsystem/control unit determines to what extent, if any, the fluid inflow and fluid outflow should be increased or decreased while maintaining the desired pressure and outputs the appropriate signal(s) to adjust one of or both of the fluid inflow and the fluid outflow. For example, the fluid control subsystem/control unit causes the operation of the respective pumps(s) to be adjusted so as to provide the desired flow. This determining process preferably is based on an algorithm that relates an operating load of the resection device 150 to a fluid inflow and/or outflow.

When the resection device 150 or other surgical instrument embodies an electric motor to power the device (e.g., motor causes the rotating cutting implement to rotate) the motor control subsystem/ control unit (110b/102b) more particularly monitors the current usage of the motor and provides an output signal representative of the current being provided to the motor. Using an algorithm or other process, the fluid controller or control unit 102a processes this current signal, determines the appropriate fluid inflow and fluid outflow for this current and, if necessary, adjusts fluid inflow and fluid outflow (120a, b) based on the determined/measured current.

In more particular aspects, fluid control is based on a motor load measurement of the surgical resection device 150 and fluid control also can be regulated by using input from flow and pressure sensors as well as the variable load of the motor in the form of direct current measurement. In this example, motor torque is related to or is a function of the supplied current such as shown, for example, in FIG. 5. When the surgical device is resecting (e.g., cutting or trimming tissue), flow may be increased when current demand is higher due to increased cutting torque. This is accomplished through a flow versus torque function and algorithm. In addition, or alternatively, the speed (RPM) of the motor is used to correlate the inputs and formulate an appropriate outflow. The individual contributors are processed to accomplish the goal of maintaining internal joint pressure. In yet further aspects, the flow control subsystem/control unit is configured and arranged (e.g., include software code segments) to provide overpressure safe-guards to prevent for example, the deleterious extravasation of fluid into the patient.

In yet further aspects, when the resection device or other surgical instrument is turned off or stops functioning, a signal is outputted from the device control subsystem/control unit (110b/102b) to the flow control subsystem/control unit (110, 102a). Upon receipt of this signal, the flow control subsystem/control unit automatically undertakes a process for securing fluid inflow and/or fluid outflow. In a more particular aspect, the flow control subsystem/control unit reduces such inflow and outflow in a time wise fashion or step wise fashion over time so that the flow of fluid continues at a periodic reducing rate until it is stopped.

Figure 3:
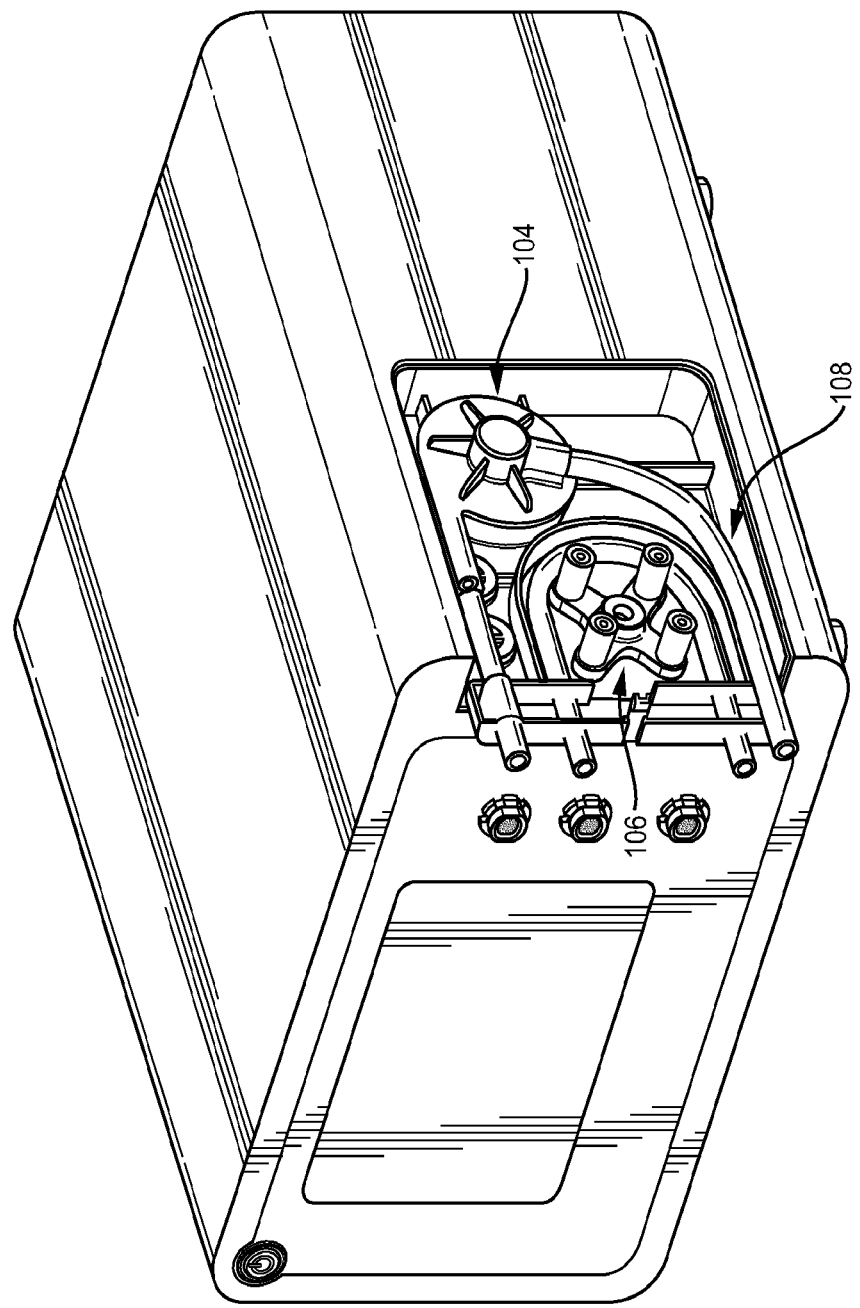
FIG. 3 is an illustrative control unit for providing motor and fluid control according to the present invention.

In more particular aspects the fluid control unit is configured to include the structure for the inflow pump 104 and the outflow pump 106 (or other suction source) and uses a disposable cassette tube-set 108 as is generally known in the art to fluidly couple the inflow pump and the outflow pump (or other suction source) to the respective fluid discharge line and the suction line and correspondingly the fluid inflow and fluid outflow. An illustration of such an exemplary fluid control unit 202b embodying such a structure and use of a cassette tube-set 108 is shown in FIG. 3.

Figure 4A:
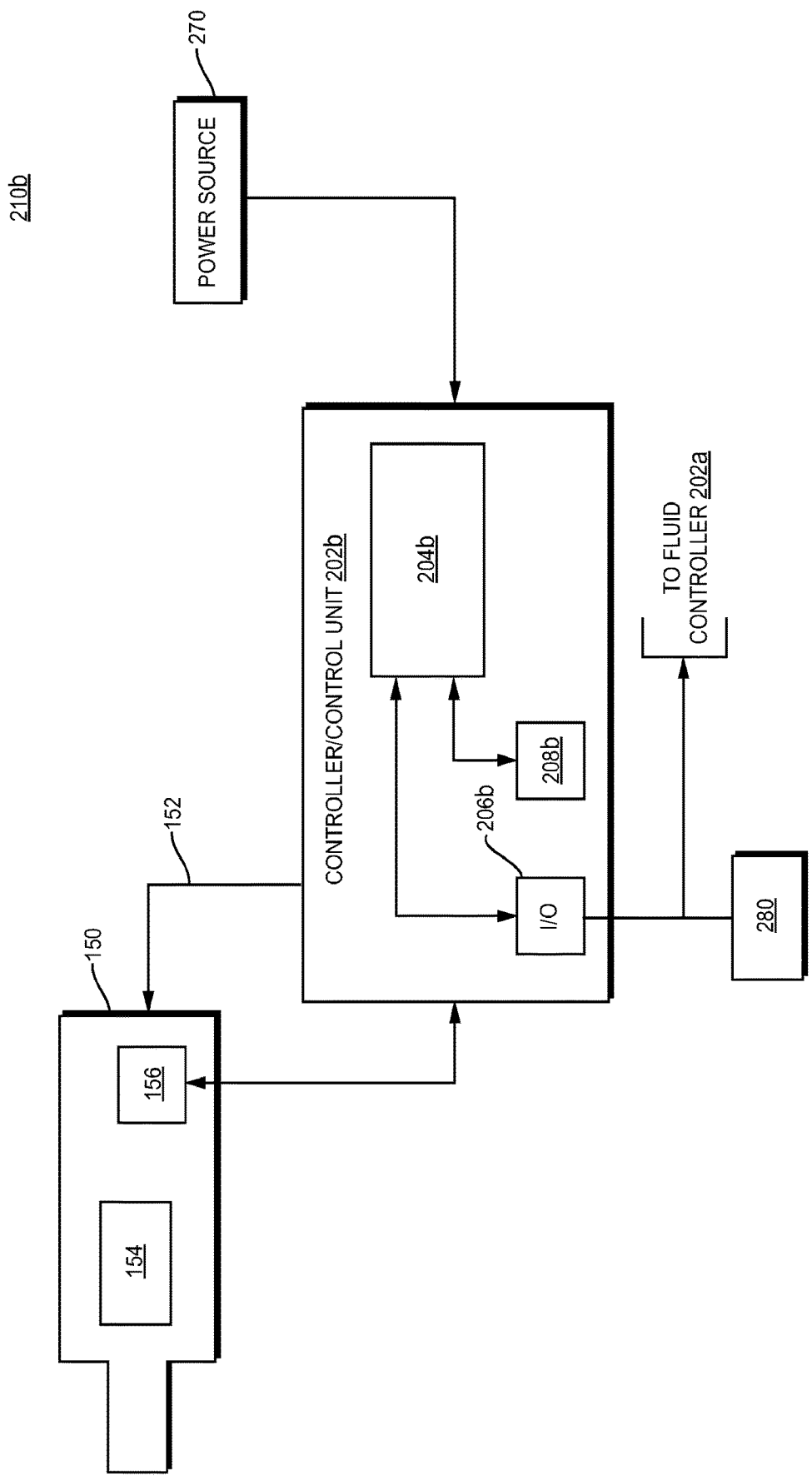
FIG. 4A is a block diagram of an exemplary schematic of a device control system according to the present invention.

Referring now to FIG. 4A there is shown a block diagram of an exemplary schematic of a device control sub system 210b according to the present invention. Such a subsystem includes a controller or control unit 202b that is operably coupled to a power source 270 and the resection device 150. As indicated above, the resection device 150 is operably coupled to the control unit 202b by means of a motor control cable 152. The control unit 202b includes a computing mechanism 204b such as a microprocessor, digital signal processor, an application specific integrated circuit or the like, which computing mechanism receives inputs and provides outputs controlling operation of the resection device 150 and operational parameters relating to operation of the resection device. Such a computing mechanism 204 also embodies a software program including instructions, criteria, data and/or code segments for carrying out the methods, method steps and operations described herein.

The power source 270 is coupled to the control unit 202b so as to supply power to the control unit and/or the resection device 150. More specifically, the power source 270 is selectively and adjustably coupled electrically to the resection device 150 so as to be under the control of the control unit 202/computing mechanism 204b. As herein described above, such a control unit controls the electrical power being supplied to the motor 154 of the resection device 150 so as to thereby control the rotational speed of the motor and thus the rotational speed of the surgical tool coupled to the resection device that is used for processing tissue according to the surgical procedure. More particularly, the control unit 202b, more particularly the computing mechanism 204b, controls the electrical power being supplied to adjust the power upwards or downwards to suit that desires of the surgeon as well as being responsive to changing conditions.

The resection device 150 also is configured with at least a motor sensor 156 for detecting or determining the rotational speed of the motor 154. As described herein, the output of the motor sensor can be used in determining if there are changing operational conditions. In addition, the control unit 202b can be further configured so as to include a power sensor 208b such as a current sensor to detect the operational current or power being drawn by the motor. The control unit 202b/computing mechanism 204b using one or more of these inputs can determine if there is a changing condition that in turn requires adjustment of the power to the motor. As described herein, such changing conditions also can be used by the device control unit 202b or the fluid control unit 202a to determine if the changing conditions also require and adjustment to the inflow and/or outflow flow levels. In the case where the determination is made by the fluid control unit 202a, the computing mechanism 204b causes the appropriate information to be outputted to the fluid control unit 202a via an input/output (I/O) device 206b. Such an I/O device 206b also can comprise any one or more of devices that can be used operably couple the computing mechanism 204b to an external device(s) 280. Such coupling can be used to update operational information as well as coupling the computing mechanism 204b to an external storage or computing device.

Such a control unit 202b can be arranged so as form in part a general purpose computer as is known in the art that has a computer processor, and memory, connected by a bus 26. The memory is a relatively high speed machine readable medium and includes volatile memories such as DRAM, and SRAM, and non-volatile memories such as, ROM, FLASH, EPROM, EEPROM, and bubble memory. Also connected to the bus can be secondary storage, external storage, output devices such as a monitor or display, input devices such as a keyboard and mouse. Such secondary storage includes machine-readable media such as hard disk drives, magnetic drum, and bubble memory. The external storage includes machine-readable media such as floppy disks, removable hard drives, magnetic tape, CD-ROM, and even other computers, possibly connected via a communications. In addition to the software program(s) executing the methods, etc. of the present invention, the computer software being executed can include operating systems. Executable versions of computer software can be read from a non-volatile storage medium such as external storage, secondary storage, and non-volatile memory and loaded for execution directly into the volatile memory, executed directly out of non-volatile memory, or stored on the secondary storage prior to loading into the volatile memory for execution.

Figure 4B:
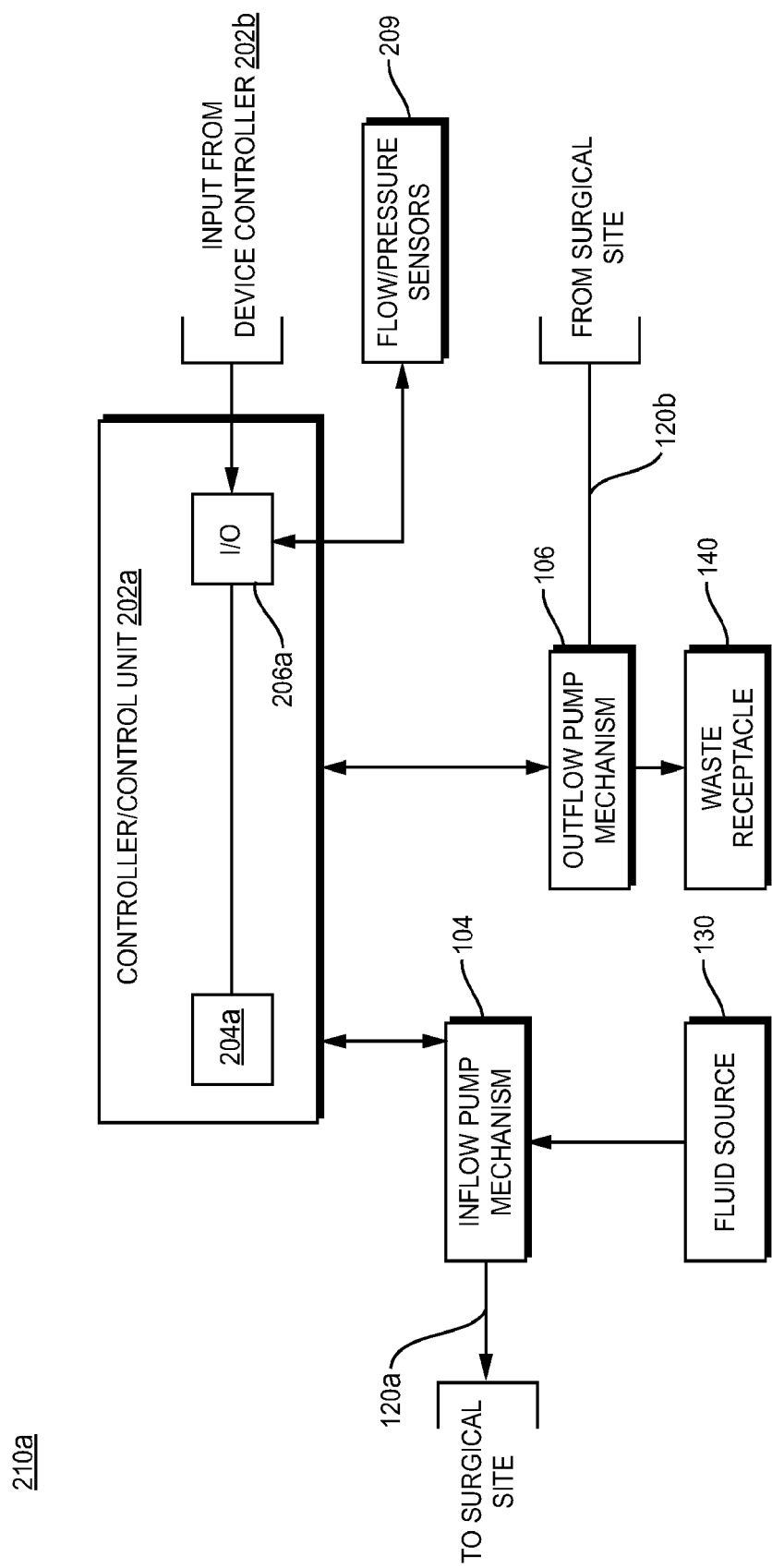
FIG. 4B is a block diagram of an exemplary schematic of a combined fluid and fluid control system according to one embodiment of the present invention.

Referring now to FIG. 4B, there is shown a block diagram of an exemplary schematic of a combined fluid and fluid control system 210a according to one embodiment of the present invention. In the illustrated embodiment, for convenience the inflow and outflow files are shown as going to/from the surgical site but does not include the specific device or mechanism which fluidly couples the inflow and outflow lines respectively to the surgical site.

As described herein, such a fluid control system 210a, more particularly, the control mechanism 202a thereof, is configured and arranged so as to automatically control the levels of fluid inflow and outflow (e.g., increasing or decreasing levels of flow) so as to maintain desired operational conditions as well as automatically adjusting the levels of fluid inflow and outflow to accommodate changing operational conditions of the resection device 150 that are related to potential changes in the amount of debris being generated during the surgical procedure. As further described herein such a fluid control system 210a (e.g., computing mechanism 204a) can receive operation input from the device control system 210b/device control unit 202b which can be used to determine how and how much to automatically adjusting the levels of fluid inflow and outflow. Reference shall be made to the discussion regarding FIG. 4A as to details for the control mechanism 202a and the computing mechanism 204a thereof unless otherwise provided below.

Such a fluid control mechanism 202a, more particularly the computing mechanism 204a thereof, is operably coupled to the inflow pump mechanism 104 and the outflow pump mechanism 104 so as to thereby control the operation of the respective pump mechanism. More particularly and as described herein, the computing mechanism 204a controls the operation of the respective pump mechanism 104, 106 so as to thereby control the flow of one or both of the inflow or outflow so as to maintain desired pressure and flow conditions in and about the surgical site. In addition, the computing mechanism 204a controls the operation of the respective pump mechanism 104, 106 so the pressure and flow conditions in and about the surgical site do not exceed set conditions that could lead to an unwanted condition(s) as described herein. Further, the computing mechanism 204a controls operation of the respective pump mechanism 104, 106 so as to automatically change the flow of one or both of the inflow or outflow responsive to changed operational parameters (e.g., motor load) so as to adjust for increasing levels of effluent production from the surgical site during the surgical procedure.

Also coupled to the control unit 202a and the computing mechanism 204a, can be various flow and/or pressure sensors 209 that provide an input(s) to the computing mechanism. These various flow and pressure inputs are used by the computing mechanism 204a to control the flow of the inflow and/or outflow to maintain the desired operational conditions, to prevent unwanted operational conditions and to adjust operational parameters to accommodate changing operational conditions involving the amount and/or kind of effluent being produced. Such flow and pressure sensors can be any of a number of sensors as are known in the art and appropriate for the intended use. While such sensors can be arranged so as to be in fluid connection with the various fluid lines it also is within the scope of the present invention to use an external pressure sensor (e.g., external pressure sensor).

As indicated hereinabove, the computing mechanism 204a of the fluid control device receives inputs from the device control unit 202b which are used by the software program being executed on the fluid control mechanism, more particularly the computing mechanism 204a thereof, to determine if there are present changed operational conditions for at least the resection device 150 and further that these changed conditions warrant a change in the flow of one or both of the fluid inflow or fluid outflow (increase or decrease). In other words and as described herein, the flow of the inflow and/or outflow can be automatically adjusted to deal with changing conditions associated with increasing or decreasing changes in the effluent being produced during a given surgical procedure. As also described herein the computing mechanism 204a of the fluid control device also can receive pressure and/or flow inputs in combination with any detected change in operational conditions for the resection device 150 and using these combined inputs to determine what change in the flow of one or both of the fluid inflow or fluid outflow (increase or decrease) to make.

Figure 4C:
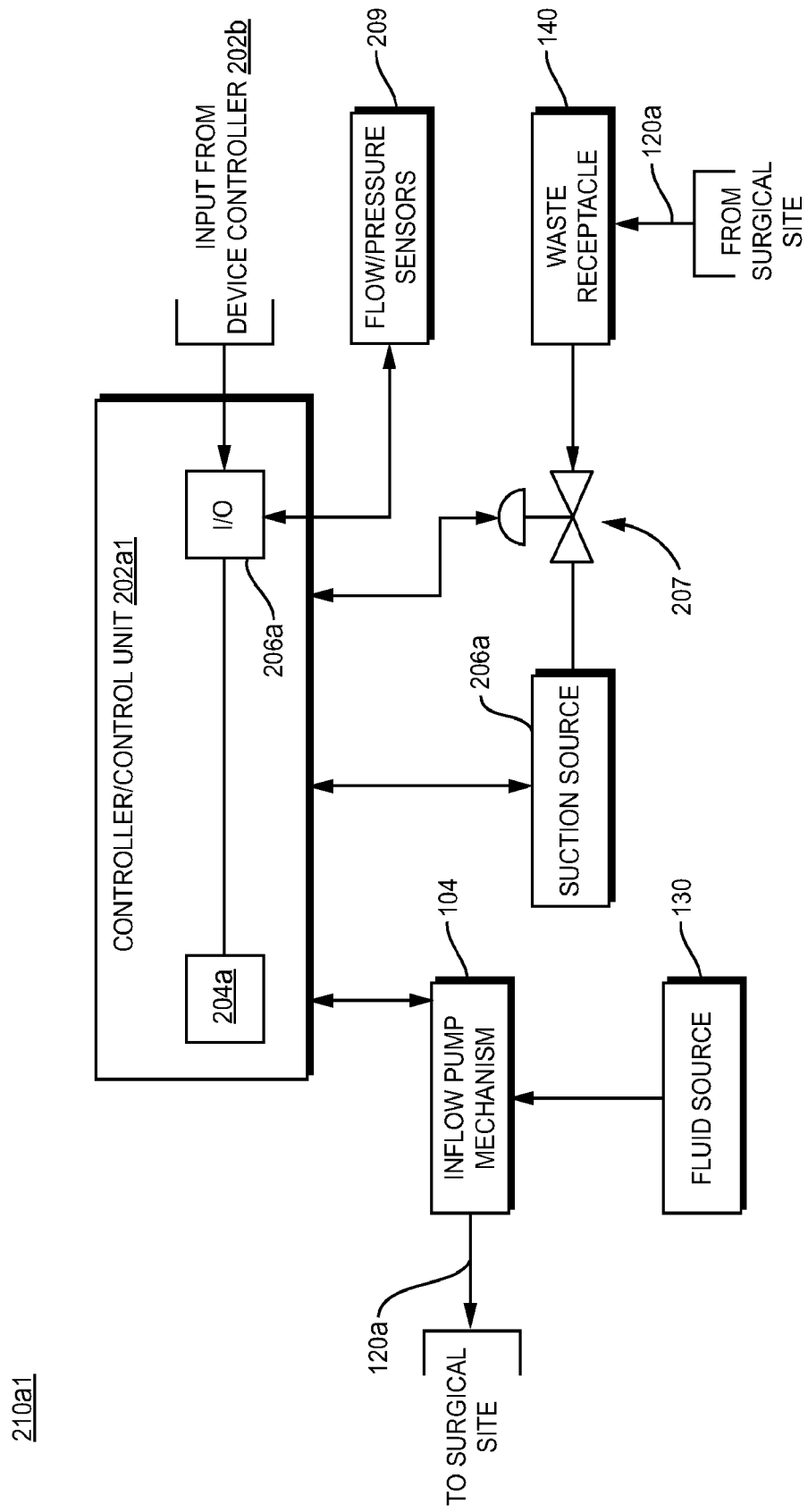
FIG. 4C is a block diagram of an exemplary schematic of a combined fluid and fluid control system according to another embodiment of the present invention.

Referring now to FIG. 4C, there is shown a block diagram of an exemplary schematic of a combined fluid and fluid control system 210a1 according to another embodiment of the present invention. Reference shall be made to the foregoing discussion regarding FIG. 4B for common elements. In the illustrated embodiment, for convenience the inflow and outflow 120a,b are shown as going to/from the surgical site but do not include the specific device or mechanism which fluidly couples the inflow and outflow lines respectively to the surgical site. Reference shall be made to the discussion regarding FIGS. 4A and B as to details for the computing mechanism 204a1 unless otherwise provided herein.

As with the exemplary fluid control system 210a of FIG. 4B, a fluid control system 210a1 according to this embodiment, more particularly, the control unit 202a1 thereof, is configured and arranged so as to automatically control the levels of fluid inflow and outflow so as to maintain desired operational conditions as well as automatically adjusting the levels of fluid inflow and outflow to accommodate changing operational conditions of the resection device 150 that are related to potential changes in the amount of debris being generated during the surgical procedure. As further described herein such a fluid control system 210a1 can receive operation input from the device control system 210b/device control unit 202b which can be used to determine how and how much to automatically adjusting the levels of fluid inflow and outflow.

Reference shall be made to the discussion regarding FIGS. 4A and 4B as to details for the computing mechanism 204a unless otherwise provided herein.

In this embodiment, the fluid outflow comprises a valve 207 and suction source 206a or suction mechanism that are fluidly coupled to the waste receptacle 140 so as to thereby control the suction pressure on the waste receptacle and thus on the fluid outflow 120a. In this embodiment the control unit 202a1 and the computing mechanism 204a1 thereof are operably coupled to at least the valve 207 (e.g., a control valve) and are further configured and arranged so as to adjust the suction pressure being asserted within the waste receptacle by controlling the valve (e.g., amount of opening or closing of the valve). Alternatively, the control unit 202a1 and the computing mechanism 204a1 thereof are operably coupled to one or both of the valve 107 and the suction source/mechanism 206a so as to thereby control the desired suction pressure developed within the waste receptacle.

In yet further aspects, the one or more control units or the appropriate control sub-system 110, 210 is further configured and arranged so that volumetric flow rate data is acquired (e.g., using a flow sensor) and used to regulate pump speed and joint pressure. In addition, the system can be further configured and arranged so as to include servo controlled outflow valves, which would be used to maintain pressure and flow rate. In either of these cases, the control unit(s) would be configured to include the appropriate instructions and criteria to regulate pump speed and joint pressure and/or controlling the servo-controlled valves also to maintain pressure and flow rate.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

According to further aspects of the present invention, there are featured methods for repairing tissue by providing such a closed loop surgical system and automatically controlling fluid input and fluid suction as well as automatically adjusting such fluid flow and suctioning based on a signal(s) from the device controller 102a, b and 202a,b. More specifically such methods also include providing such a closed loop surgical system which is capable of (a) adjusting fluid flow responsive to changes in the loading of a resection device, more particularly (b) automatically sensing a load change for a given resection device during the conduct of the surgical procedure and automatically changing (increasing or decreasing) fluid flow responsive to such a load change; or (c) automatically determining current flow changes to an electric motor of the resection device, relating these current changes to a load change and automatically changing (increasing or decreasing) fluid flow (inflow and/or outflow) responsive to such a current or load change.

Figure 6:
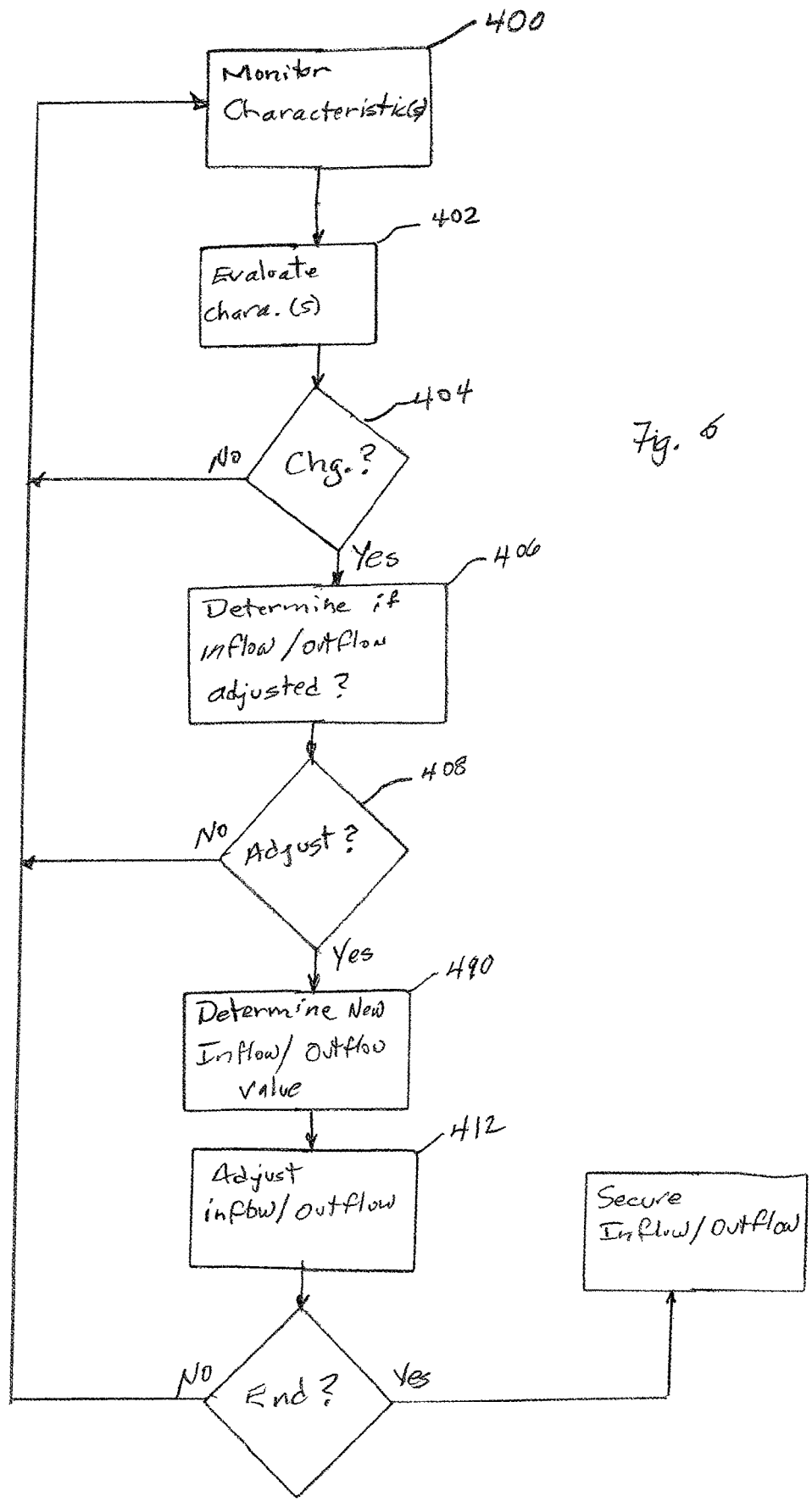
FIG. 6 is a high level flow diagram illustrating the fluid and device control according to the present invention.

Referring now to FIG. 6 there is shown an illustrative exemplary method according to another aspect of the present invention. After the surgeon has begun the surgical procedure including after the resection device 150 is operational, such a method includes monitoring at least one operational parameter/characteristic, Step 400 and evaluating the detected parameter/characteristic, Step 402. The detected parameter/characteristic is evaluated, Step 404, to determine if the evaluated operational parameter/characteristic represent a changing value. For example, the electrical power (e.g., current) is monitored to detect changes in power consummation and determine of this change maybe indicative of a changing load on the motor of the resection device.

In yet further embodiments, such monitoring can include monitoring more than one operational parameter and/or characteristic such as flow, current and pressure, evaluating each of the parameters and determine whether any of the one or more parameters are changing.

If there is no change detected (No, Step 404), then the process returns to monitoring the parameters (Step 400). If there is a change detected (Yes, Step 404), then the process proceeds with evaluating the change characteristic/parameter to determine if the inflow/outflow should be adjusted, Step 406. For example, are the operational conditions unacceptable (e.g., over pressure condition of the joint) or should the flow rate be adjusted to compensate for changing load conditions or changing effluent conditions.

If there is no need to adjust (No, Step 408), then the process returns to monitoring the parameters (Step 400). For example, while there may be a change in the operational parameter it could be determined that the change is such that it is not of a sufficient change that would warrant changing flow rates. If there is a change detected (Yes, Step 408), then the process proceeds with determining the appropriate action to take, Step 410. More particularly, the respective computing mechanism 204a determines how much the inflow and/or outflow should be adjusted. The respective computing mechanism then would determine what action the related device should take to accomplish the desired change, Step 412. For example, the computing mechanism would provide an output to the respective positive drive pump or device to adjust (increase or decrease) the present flow rate to the determined new value.

While monitoring for changing conditions, also monitored is the operational status of the resection device to determine if the resection device is no longer in operation (i.e., has operation ended), Step 414. If operation has not ended (No, Step 400) then the process returns to monitoring the parameters (Step 400). If operation has ended (Yes, Step 414) then the computing mechanism 204a causes the inflow and outflow subsystems to be appropriately secured or put in an appropriate condition, Step 416. For example, the inflow and outflow subsystems can be returned to a no flow condition (shutdown) or they can be returned to a standby condition. Alternatively, the systems can be operated so as the flows are gradually reduced to the no-flow or stand by conditions such as by reducing flows in a time wise or step wise fashion.

In yet further aspects of the present invention, the present invention also features any of a number of controllers including computing mechanisms and a software program for execution on the computing mechanism. Such software includes instructions, data, code segments and criteria for performing the various processes and method steps described herein above. Further, the flow charts herein illustrate the structure of the logic of the present invention as embodied in computer program software for execution on a computer, digital processor or microprocessor. Those skilled in the art will appreciate that the flow charts illustrate the structures of the computer program code elements, including logic circuits on an integrated circuit that function according to the present invention. As such, the present invention is practiced in its essential embodiment(s) by a machine component that renders the program code elements in a form that instructs a digital processing apparatus (e.g., computer) to perform a sequence of function step(s) corresponding to those shown in the flow diagrams.

Although preferred embodiments of the invention have been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A closed loop surgical system, comprising:
a fluid control subsystem including a fluid controller that is configured to control a fluid inflow to a surgical site and a fluid outflow from the surgical site, one or both of the fluid inflow or the fluid outflow being controlled so as to maintain a preselected pressure within the surgical site; and
a device control subsystem including a device controller that is configured to control a surgical device and automatically determine an amount of current flow to and a motor speed of an electric motor of the surgical device;
wherein one of the fluid controller or the device controller determines from the amount of current flow and the motor speed if operational conditions for the surgical device have changed and determines a corresponding flow change to one or both of the fluid inflow or the fluid outflow in response to the operational conditions being changed; and
wherein the fluid controller is further configured to cause one or both of the fluid inflow or the fluid outflow to be one of increased or decreased based on the corresponding flow change.

2. The closed loop surgical system of claim 1, wherein the fluid controller is further configured to maintain the preselected pressure by utilizing empirically correlated load measurements and the motor speed, based on the amount of current flow, to the surgical device.

3. The closed loop surgical system of claim 1, further comprising an inflow pump, an outflow pump and a fluid source,
wherein the fluid source is coupled to the inflow pump;
wherein each of the inflow and outflow pumps are fluidly coupled to the surgical site; and
wherein the fluid controller controls operation of one or both of the inflow pump and the outflow pump so as to at least maintain the preselected pressure in an area at the surgical site.

4. The closed loop surgical system of claim 3, wherein the fluid controller is configured to automatically adjust one or both of the fluid inflow or the fluid outflow responsive to a load change of the surgical device.

5. The closed loop surgical system of claim 4, wherein the device controller is configured to automatically sense the load change for the surgical device during a surgical procedure.

6. The closed loop surgical system of claim 1, wherein the fluid controller is further configured to cause one or both of the fluid inflow or the fluid outflow to be decreased in a step wise fashion over time in response to a stoppage of the surgical device.

7. The closed loop surgical system of claim 1, wherein the fluid controller is further configured to determine the corresponding flow change to one or both of the fluid inflow or the fluid outflow based on a motor torque of the electric motor.

8. The closed loop surgical system of claim 1, wherein the amount of current flow determined by the device controller varies due to a changing motor load.

9. The closed loop surgical system of claim 1, wherein the device control subsystem is further configured to detect the motor speed of the electric motor using a motor sensor of the surgical device.

10. The closed loop surgical system of claim 1, wherein the one of the fluid controller or the device controller is further configured to provide over pressure safe-guards.

11. The closed loop surgical system of claim 1, wherein the device control subsystem is further configured to control the amount of current flow to the electric motor to maintain the motor speed of the electric motor.

12. A closed loop surgical system comprising:
a fluid source for supplying a fluid;
an inflow pump fluidly coupled to the fluid source and to a surgical site for supplying the fluid to the surgical site;
an outflow pump fluidly coupled to the surgical site for removing the fluid from the surgical site;
a fluid control subsystem including a fluid controller coupled to the inflow pump and the outflow pump, the fluid controller configured to control inflow of the fluid to the surgical site and outflow of the fluid from the surgical site, both of the inflow of the fluid and the outflow of the fluid being controlled so as to maintain a preselected pressure within the surgical site;
a device control subsystem including a device controller that is configured to control a surgical device and monitor an amount of current flow to and a motor speed of an electric motor of the surgical device;
wherein one of the fluid controller or the device controller determines from the amount of current flow and the motor speed if operational conditions for the surgical device have changed and determines a corresponding flow change to one or both of the inflow of the fluid or the outflow of the fluid in response to the operational conditions being changed; and
wherein the fluid controller is further configured to cause the one or both of the inflow of the fluid or the outflow of the fluid to be one of increased or decreased based on the corresponding flow change.

* * * * *